(12) United States Patent
Spickermann

(10) Patent No.: US 6,736,789 B1
(45) Date of Patent: May 18, 2004

(54) METHOD AND DEVICE FOR EXTRACORPOREAL BLOOD TREATMENT WITH A MEANS FOR CONTINUOUS MONITORING OF THE EXTRACORPOREAL BLOOD TREATMENT

(75) Inventor: Reiner Spickermann, Wasserlosen/Burghausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/176,744

(22) Filed: Oct. 21, 1998

(30) Foreign Application Priority Data

Oct. 21, 1997 (DE) .......................................... 197 46 377

(51) Int. Cl.[7] .......................... A61M 37/00; A61M 1/14; C02F 1/44; B01D 35/14; B01D 24/00
(52) U.S. Cl. ...................... 604/5.01; 604/4.01; 422/44; 128/DIG. 3; 210/645; 210/646; 210/739; 210/746; 210/87; 210/90; 210/321.6; 210/418
(58) Field of Search ...................... 604/4–6, 66, 29–31, 604/65, 47, 27, 4.01, 5.01; 422/44–48; 128/DIG. 3

(56) References Cited

U.S. PATENT DOCUMENTS

| 3,421,497 A | * | 1/1969 | Chesnut et al. | |
| 3,946,731 A | * | 3/1976 | Lichtenstein | 210/87 |
| 4,464,172 A | | 8/1984 | Lichtenstein | |
| 4,466,804 A | * | 8/1984 | Hino | 604/4.01 |
| 4,598,697 A | * | 7/1986 | Numazawa et al. | 604/4 |
| 4,710,164 A | | 12/1987 | Levin et al. | |
| 5,178,763 A | * | 1/1993 | Delaunay | 210/644 |
| 5,237,997 A | * | 8/1993 | Greubel et al. | 600/485 |
| 5,293,874 A | * | 3/1994 | Takahashi et al. | 600/500 |
| 5,476,444 A | * | 12/1995 | Keeling et al. | 604/4 |
| 5,564,427 A | | 10/1996 | Aso et al. | |
| 5,584,299 A | * | 12/1996 | Sakai et al. | 128/681 |
| 5,876,348 A | * | 3/1999 | Sugo et al. | 128/681 |
| 5,921,936 A | * | 7/1999 | Inukai et al. | 600/490 |
| 6,527,728 B2 | * | 3/2003 | Zhang | 600/500 |

FOREIGN PATENT DOCUMENTS

| DE | 35 33 912 | | 9/1989 |
| EP | 0 443 267 A1 | * | 8/1991 |
| WO | WO 89/08424 | | 9/1989 |

OTHER PUBLICATIONS

Psychophysiology, vol. 13, No. 1, 1976.

* cited by examiner

Primary Examiner—Patricia Bianco
(74) Attorney, Agent, or Firm—Kenyon & Kenyon

(57) ABSTRACT

A method and a device for continuous, noninvasive monitoring of an extracorporeal blood treatment, a patient's blood pressure or a quantity that correlates with the blood pressure is measured and compared with a predetermined limit value. If the measured blood pressure or its relative change drops below the predetermined limit value, an activation or deactivation signal is generated to initiate an intervention in the treatment sequence. The blood treatment machine therefore has a control unit. The continuous, noninvasive measurement of blood pressure is based on a determination of the propagation rate or transit time of the pulse waves produced by the patient's cardiac contractions and their propagation through the arterial system. To determine the pulse wave velocity or transit time, the blood treatment machine has an electrocardiograph and a device for detecting the pulse waves at a location on the patient remote from the heart.

18 Claims, 3 Drawing Sheets

METHOD AND DEVICE FOR EXTRACORPOREAL BLOOD TREATMENT WITH A MEANS FOR CONTINUOUS MONITORING OF THE EXTRACORPOREAL BLOOD TREATMENT

FIELD OF THE INVENTION

The present invention concerns a method for continuous monitoring of an extracorporeal blood treatment, especially a method whereby blood in an extracorporeal circulation flows through a blood chamber of a dialyzer or hemofilter subdivided by a semipermeable membrane into the blood chamber and a dialysis fluid chamber or a hemofiltrate chamber. In addition, the present invention concerns a machine for extracorporeal blood treatment with a device for continuous monitoring of the extracorporeal blood treatment.

BACKGROUND OF THE INVENTION

Acute emergencies during dialysis demand immediate action. Such emergencies may be caused by the blood treatment itself or they may occur independently of the blood treatment. A drop in blood pressure is one of the main complications during a dialysis treatment and/or hemofiltration. The most common cause of such an incident is hypovolemia due to excessive withdrawal of fluid. Other causes may include concentration changes, temperature variations or biocompatibility reactions (Journal für das Nephrologische Team [Journal for the Nephrological Team], vol. 3 (1996), p. 113).

There are known hemodialysis machines having a plug-in unit which permits indirect measurement of a patient's systolic and diastolic blood pressure. This plug-in unit is a conventional sphygmomanometer with an inflatable rubber cuff connected to a manometer. To measure systolic blood pressure, the cuff pressure is increased slowly until the pulse is no longer palpable. The systolic pressure can be measured by subsequently reducing the cuff pressure slowly until the first pulse beat can be palpated. If the cuff pressure drops below the systolic blood pressure, vascular noises occur in synchronization with the pulse, but cannot be detected on reaching the diastolic pressure as the cuff pressure is released further. The measurement is fully automatic with an acoustic sensor, a pressure sensor and an electric air pump for inflating the cuff. One disadvantage is that with the known dialysis machines having a conventional sphygmomanometer, a patient's blood pressure is monitored only at certain intervals. There is usually an interval of approximately 10 to 15 minutes between two measurements. Shorter intervals in the minute range are possible, but this would be unreasonable for the patient during a hemodialysis treatment, usually lasting for several hours. Within this period of time, signs of a cardiovascular problem may remain undetected, and the subsequent measurement may be too late to initiate appropriate countermeasures so that treatment can be continued without interruption.

A method is known for continuous, noninvasive monitoring of changes in blood pressure on the basis of analysis of the pulse wave transit time (Psychophysiology, vol. 13, no. 1, 1976). With the known method, the blood pressure is determined on the basis of the transit time required for a wave produced by a cardiac contraction to reach a certain site in the body. Various studies have confirmed the fact that there is an approximately linear relationship between the pulse wave transit time and the systolic and diastolic blood pressure or the mean blood pressure.

OBJECTS OF THE INVENTION

The object of the present invention is to provide a method of continuous monitoring of an extracorporeal blood treatment that will reduce the risk of complications due to a drop in blood pressure during the blood treatment. This object is achieved according to invention using a method of continuously monitoring a subject's extracorporeal blood treatment comprising the steps of: providing blood to be treated to a blood treatment device in an extracorporeal blood path; determining a pulse wave velocity or pulse wave transit time; determining a blood pressure value by correlating the pulse wave velocity or pulse wave transit time with a predetermined blood pressure value or value correlating to blood pressure for the pulse wave velocity or pulse wave transit time; comparing the blood pressure value with a predetermined blood pressure limit; and generating a signal to initiate a change in the extracorporeal blood treatment when the blood pressure value falls outside the predetermined blood pressure limit.

Another object of the present invention is to create a device for extracorporeal blood treatment, where the risk of complications due to a drop in blood pressure during the blood treatment is reduced. This object is achieved with a blood treatment device according to the present invention having an extracorporeal blood path connecting the subject to the blood treatment device, the blood treatment device having an inlet and an outlet, the extracorporeal blood path carrying blood from the subject to the blood treatment device inlet and from the blood treatment device outlet back to the subject. The blood treatment device further comprises a measurement device for continuously determining the subject's pulse wave velocity or pulse wave transit time. A correlation device is connected to the measurement device and the correlation device is adapted to correlate the pulse wave velocity or pulse wave transit time with a predetermined blood pressure value or value correlating with blood pressure. A comparison device is connected to the correlation device and the comparison device is adapted to compare the blood pressure value or value correlating with blood pressure with a predetermined blood pressure limit and generate a signal when the blood pressure value is outside the blood pressure limit. A control unit is connected to the comparison device and the control unit adapted to initiate a change in the subject's extracorporeal blood treatment in response to the signal.

With the method and the device according to the present invention, the blood pressure or a quantity correlating with the patient's blood pressure is monitored continuously during the blood treatment. If the measured value drops greatly, a control signal is generated to initiate a measure in the treatment process to counteract the drop in blood pressure. Since the measurement is performed continuously, a drop in blood pressure can be detected immediately and counteracted immediately.

This continuous, noninvasive blood pressure measurement is based on detection of the propagation rate of the pulse waves produced by contractions of the cardiac contractions propagating through the patient's arterial system. Instead of the propagation rate, the transit time of the pulse waves can be determined over a segment of the vascular system of a predetermined length.

It is advantageous that the patient is unaware of the monitoring of the blood treatment, especially since no tedious blood pressure measurement using an inflatable rubber cuff is necessary at certain intervals.

Blood treatment machines are understood to include all machines in which the blood of a patient or a donor is subjected to a certain treatment in an extracorporeal system. Blood treatment machines include not only machines for hemodialysis or hemofiltration but also the known cell separators in which a donor's blood is centrifuged to separate it into its components.

For continuous measurement of blood pressure, the pulse wave transit time is preferably determined. The means for determining the pulse wave transit time include a device for recording an electrocardiogram and a device for detecting the pulse waves at a location remote from the patient's heart, in particular a fingertip or the earlobes, as well as a device for determining the time between the time at which the so-called R wave (maximum ventricular depolarization) occurs in the electrocardiogram and the time when the pulse wave is detected at a location on the patient's body which can be attributed to the cardiac contraction. In an especially advantageous embodiment, the device for detecting the pulse waves may also be the arterial pressure sensor of the extracorporeal blood circulation which is present anyway in the known blood treatment equipment.

With the method and the device according to the present invention, the blood pressure is deduced from the pulse wave transit time. The means for determining the blood pressure or a quantity correlating with the blood pressure include a computer unit in which the blood pressure is calculated from the pulse wave transit time on the basis of a linear correlation. For relative monitoring of the blood pressure, it is sufficient to determine a quantity that correlates with the blood pressure, such as the pulse wave transit time. However, if absolute blood pressure values are to be measured, a calibration can be performed with a known sphygmomanometer.

For the case when the measured blood pressure drops below a predetermined limit or there is an excessively great change in the relative blood pressure, an activation or deactivation signal is generated to initiate an intervention in the treatment sequence. Therefore, the blood treatment machine has a control unit.

In a preferred embodiment of the blood treatment machine, a device is provided for administering a bolus, in particular a predetermined quantity of a NaCl solution, into the extracorporeal blood circulation; this is activated by the control unit when the activation or deactivation signal for initiating an intervention in the treatment sequence is generated.

In another preferred embodiment of the blood treatment machine, an acoustic and/or optical alarm generator is provided, to be activated by the control unit when the activation or deactivation signal is generated.

In an embodiment of a blood treatment machine having a balancing device and an ultrafiltration device, the ultrafiltration pump of the ultrafiltration device is deactivated by the control unit when the blood pressure drops below a predetermined limit. Ultrafiltration may be deactivated for a predetermined period of time, until the blood pressure has again risen to an acceptable level.

With a blood treatment machine in which the dialysis fluid source has a temperature stabilizing unit with which at least two different temperatures can be preset, the temperature stabilizing unit is advantageously set by the control unit at a lower temperature when the blood pressure drops below the predetermined limit.

To counteract the drop in blood pressure, the electrolyte composition, in particular $Na^+$ or $K^+$, may be altered, for example, the Na concentration may be increased. Automatic administration of blood pressure-stabilizing drugs is also possible. These interventions in the blood treatment process may also be performed automatically by the blood treatment machine.

BRIEF DESCRIPTION OF THE DRAWINGS

Two embodiments of an extracorporeal blood treatment machine are explained below with reference to the drawings, which show.

DETAILED DESCRIPTION OF THE PREFERRED EMBODIMENT

Figure 1:
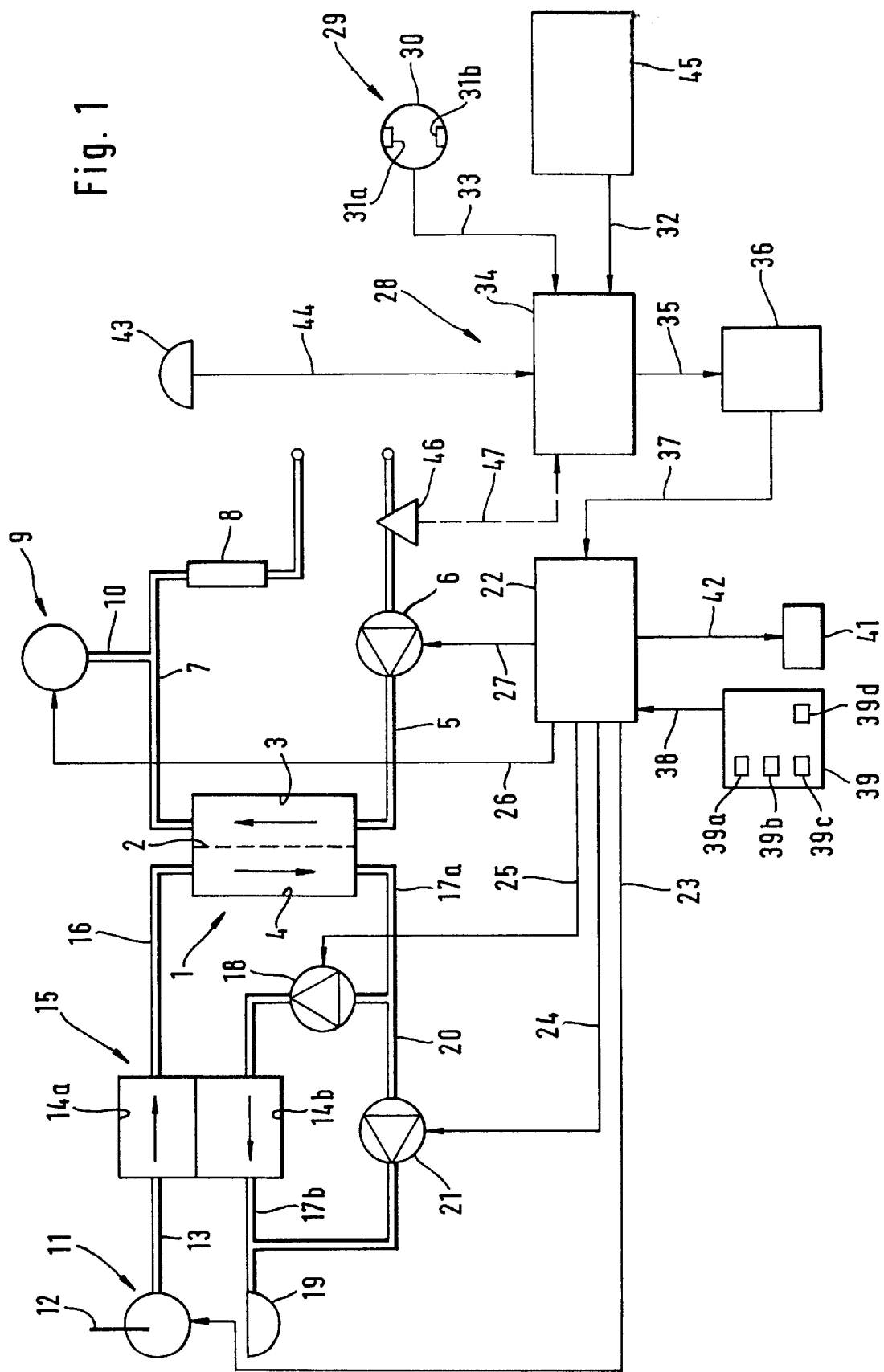
FIG. 1 a schematic diagram of a hemodialysis machine with a device for noninvasive, continuous monitoring of blood pressure.

The hemodialysis machine has a dialyzer 1 separated into a blood chamber 3 and a dialysis fluid chamber 4 by a semipermeable membrane 2. The inlet to the blood chamber is connected to one end of a blood inlet line 5 to which a blood pump 6 is connected, whereas the outlet of blood chamber 3 is connected to one end of a blood outlet line 7 which is in turn connected to a drip chamber 8. The extracorporeal blood circulation also has a device 9 to automatically administer a bolus, especially physiological NaCl solution (typically 200 mL) or online-filtered substituate solution at a typical replacement rate of 150 mL/min. The bolus is administered to the patient through an inlet line 10 connected upstream from drip chamber 8 to blood inlet line 7.

The dialysis fluid system of the hemodialysis machine includes a device 11 for processing the dialysis fluid, wherein different compositions of the dialysis fluid can be preselected (administration of electrolytes). The dialysis fluid processing device 11 has a temperature stabilizing unit 12 which adjusts the temperature of the dialysis fluid at different levels and keeps it constant. It is connected to-the-inlet of the first chamber half 14a of a balancing device 15 by a first section 13 of a dialysis fluid inlet line. The second segment 16 of the dialysis fluid inlet line connects the outlet of the first balancing chamber half 14a with the inlet of the dialysis fluid chamber 4. The outlet of the dialysis fluid chamber 4 is connected to the inlet of the second balancing chamber half 14b by the first section 17 of a dialysis fluid outlet line. A dialysis fluid pump 18 is connected to the first section 17a of the dialysis fluid outlet line. The outlet of the second balancing chamber half 14b is connected to an outlet 19 by the second section 17b of the dialysis fluid outlet line. Upstream from the dialysis fluid pump 18, an ultrafiltrate line 20, which also leads to outlet 19, branches off from the dialysis fluid outlet line 17. An ultrafiltration pump 21 is connected to ultrafiltrate line 20.

The hemodialysis machine also includes a central control unit 22 which is connected by control lines 23 through 27 to blood pump 6, dialysis fluid pump 18, ultrafiltration pump 21, device 11 for processing the dialysis fluid and device 9 for automatic administration of a bolus.

During the hemodialysis treatment, the patient's blood flows through blood chamber 3, and the dialysis fluid flows through dialysis fluid chamber 4 of dialyzer 1. Since the balancing device 15 is connected to the dialysis fluid pathway, only as much dialysis fluid can flow through the dialysis fluid inlet line 16 as can flow out through dialysis fluid outlet line 17. Fluid can be taken from the patient with ultrafiltration pump 21.

In addition, the hemodialysis machine has a device 28 for continuous, noninvasive monitoring of the extracorporeal blood treatment. Monitoring device 28 monitors the patient's blood pressure during the dialysis treatment and generates an activation or deactivation signal to initiate an intervention in the treatment sequence to counteract a sudden drop in a patient's blood pressure.

The measurement method for continuous, noninvasive monitoring of blood pressure is described in detail below with reference to FIG. 2.

This continuous, noninvasive measurement of blood pressure is based on analysis of the pulse wave velocity or pulse wave transit time. The blood pressure wave, also known as a pulse, is caused by the increase in pressure in the aorta during a systole. It is propagated through the entire arterial system at an average rate of 4 to 6 m/s. The pulse wave velocity (PWG) is the rate of propagation of the pulse wave in the arterial system. It increases at an elevated blood pressure, because the extensibility of the vascular wall decreases at high pressure. The pulse wave velocity is the quotient of the length of a certain section and the transit time of the pulse wave in traveling this section. The following relationship holds between the pulse wave velocity (PWG) and the blood pressure (Med. & Biol. Eng. & Comput. 24:248–254, 1986).

$$PWG = \sqrt{\frac{1}{\rho} \cdot \frac{dP}{dV} \cdot V} \quad (1)$$

where V is the blood volume, dV is the change in blood volume, dP is the change in blood pressure and rho is the density of the blood.

There is an approximately linear relationship between the pulse wave velocity (PWG) or the pulse wave transit time (PWLZ) and systolic and diastolic or mean blood pressure (P). The blood pressure can be calculated from the pulse wave velocity or the pulse wave transit time approximately according to the following equations:

$$P = \frac{1}{a}(PWG - b) \quad (2)$$

$$P = \frac{1}{n}(m - PWLZ) \quad (3)$$

where a and b, as well as m and n, are patient-specific constants which can be determined in comparative measurements with an absolute blood pressure measuring device.

An electrocardiogram (ECG) is recorded to determine the pulse wave transit time, and the pulse waves attributed to cardiac contractions are detected at a location in the patient's body as far away from the heart as possible, e.g., on a finger. If the patient is connected to an extracorporeal blood treatment machine, the pulse waves can also be detected with a pressure sensor in the extracorporeal circulation.

Figures 2A, 2B:
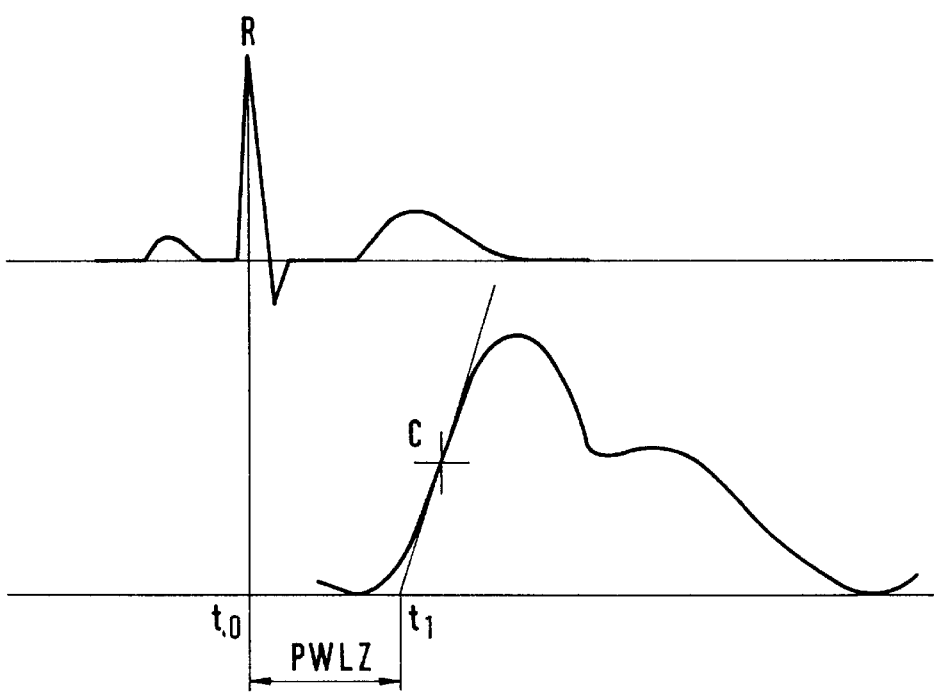
FIGS. 2a and 2b an electrocardiogram and a pulse wave signal measured on the patient's finger to determine the pulse wave transit time.

FIG. 2a shows the electrocardiogram, while FIG. 2b shows the patient's pulse wave signal attributed to the cardiac contraction. The R wave in the electrocardiogram is used as the first reference point ($t_0$) for measuring the pulse wave transit time. The increase in pressure of the pulse wave is the second reference point ($t_1$). The period of time between $t_0$ and $t_1$ is determined as the pulse wave transit time. A certain reference point C may be determined for this in the pulse wave signal, e.g., at the rising edge of the pulse wave signal.

The blood pressure can be calculated from the pulse wave transit time PWLZ=$t_1-t_0$ using the above equations, where the patient-specific constants m and n are determined by comparative measurements with a conventional sphygmomanometer.

Device 28 for monitoring the extracorporeal blood treatment has an electrocardiograph 45 for recording the electrocardiogram. These devices are known, so no further explanation is necessary. In addition, monitoring device 28 has a photoplethysmograph 29 to detect the pulse waves on the patient's finger. The photoplethysmograph has a clamp-on or glue-on sensor 30 consisting of an infrared LED 31a and a photodiode 31b. Electrocardiograph 45 and the device for detecting the pulse waves are connected to an analyzer unit 34 by data lines 32, 33. Analyzer unit 34 analyzes the electrocardiogram tracing and the finger pulse signal (FIG. 2) and determines the pulse wave transit time $t_1-t_0$ representing the relative blood pressure. The analyzer unit therefore includes a computing unit. The relative change in blood pressure is compared to a predetermined limit value in a comparator 36, which is connected by a data line 35 to the analyzer unit 34. If the relative change in blood pressure drops below the limit value, the comparator generates an activation or deactivation signal which is received by control unit 22 of the hemodialysis machine over data line 37.

The pulse waves can be determined with either photoplethysmograph 29 or a pressure sensor 46, which is provided anyway upstream of blood pump 6 for arterial pressure monitoring in the arterial blood inlet line 5 of the known hemodialysis machines. Analyzer unit 34 receives the pulse signal of pressure sensor 46 over a data line 47. Since detection of the pulse waves with pressure sensor 46 is an alternative embodiment, data line 47 is shown with dotted lines in FIG. 1. In principle, however, it is also possible to analyze both the signal of photoplethysmograph 29 and the signal of pressure sensor 46.

Control unit 22 is connected by data line 38 to input unit 39, where the user can enter which measures to be taken to counteract a sudden drop in blood pressure.

When pushbutton 39a is depressed, control unit 22 controls the temperature stabilizing unit 12 of device 11 for processing the dialysis fluid over control line 23 such that the temperature stabilizing unit sets a lower temperature for the dialysis fluid when control unit 22 receives the activation or deactivation signal from comparator 36, i.e., there has been a sudden drop in blood pressure. If switch 39b is depressed when there is a sudden drop in blood pressure, control unit 22 controls ultrafiltration pump 21 over control line 24 by stopping it. The lower dialysis fluid temperature or interruption in ultrafiltration may be continued for a predetermined length of time, but it is also possible to design the control unit so that it returns to the normal treatment sequence when the blood pressure has again stabilized, i.e., control unit 22 no longer receives the activation or deactivation signal. If the user depresses switch 39c, control unit 22 activates device 9 over control line 26 for automatic administration of a bolus, e.g., 200 mL physiological NaCl solution, when there is a sudden drop in blood pressure, so that the patient's blood pressure can stabilize again. A bolus may be administered once or, in the event the patient's blood pressure has not stabilized, it may be administered repeatedly in different quantities. If button 39d has been depressed, control unit 22 controls the dialysis fluid processing device 11 in such a way that the composition of the dialysis fluid is altered.

Monitoring device 28 also has an acoustic and/or optical alarm generator 41, which is activated by control unit 22 over a control line 42 when there is a sudden drop in blood pressure.

Control unit 22 is designed so that the measures described above for stabilizing the blood pressure can be initiated independently of one another or in combination.

To be able to measure and display absolute values for the systolic and diastolic or mean blood pressure, the hemodialysis machine has an absolute sphygmomanometer 43 with an inflatable rubber cuff connected to a manometer. Such instruments for measuring blood pressure indirectly and fully automatically are known and therefore no further description is necessary here. The output signal of sphygmomanometer 43 is sent over a data line 44 to analyzer unit 34, which determines the patient-specific constants of equation 3 from the absolute measured values in the computing unit. After the calibration, it is possible to measure the blood pressure continuously simply by determining the pulse wave transit time. The measured blood pressure values can also be displayed on a display unit (not shown). The sphygmomanometer measurement to determine absolute blood pressure values can be started automatically when the relative blood pressure values drop below the predetermined limit value.

Figure 3:
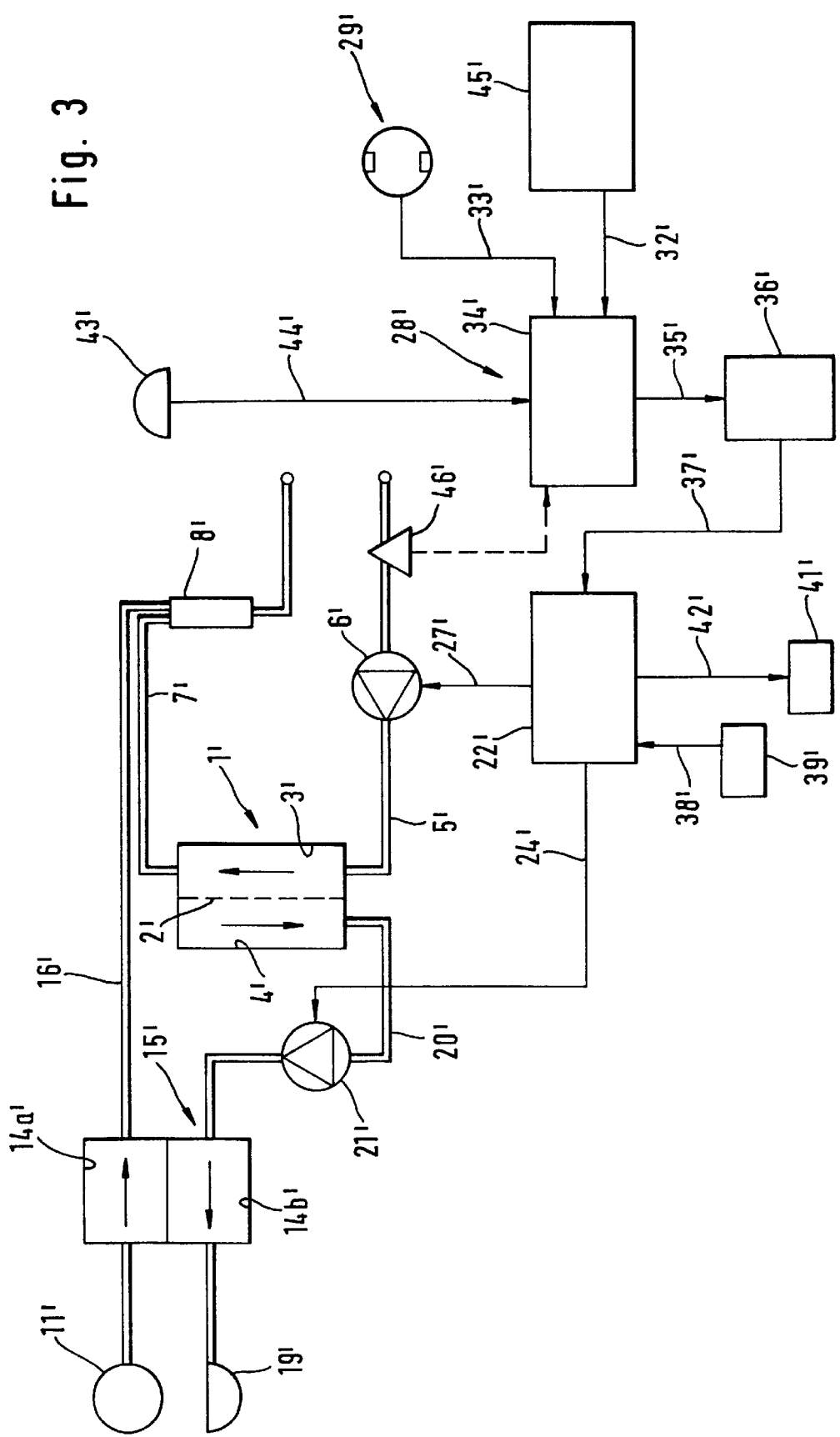
FIG. 3 a schematic diagram of a hemofiltration machine with a device for noninvasive, continuous monitoring of the blood pressure.

FIG. 3 shows a hemofiltration machine with a device for continuous, noninvasive monitoring of the extracorporeal blood treatment. The hemofiltration machine has a hemofilter 1' which is separated by a semipermeable membrane 2' into a first chamber 3' and a second chamber 4'. The inlet of the first chamber 3' is connected to one end of a blood inlet line 5' to which is connected a blood pump 6', while the outlet of the first chamber 3' is connected to one end of a blood outlet line 7', which is in turn connected to a drip chamber 8'.

The hemofiltration machine has a device 11' to supply a substituate which is connected to drip chamber 8' by a substituate line 16' which is also connected to a chamber 14a' of a balancing device 15'. A filtrate line 20' branches off from the second chamber 4' of hemofilter 1' and leads to an outlet 19' by way of the second chamber 14b' of the balancing device 15'. Upstream from balancing device 15', an ultrafiltration pump 21' is connected to filtrate line 20'.

The hemofiltration machine also includes a central control unit 22, which is connected to blood pump 6' and ultrafiltration pump 21' by control lines 27', 24'.

During hemofiltration, fluid is being removed from the patient with ultrafiltration pump 21' while substituate is being supplied to the patient.

Monitoring device 28' of the hemofiltration machine corresponds in design and function to the monitoring device of the hemodialysis machine according to FIGS. 1 through 3, so that reference can be made here to the preceding description. Monitoring device 28' has an electrocardiograph 45' for recording the electrocardiogram and a photoplethysmograph 29' for detecting pulse waves on a patient's finger. Electrocardiograph 45' and photoplethysmograph 29' are connected by data lines 32', 33' to an analyzer unit 34' which analyzes the electrocardiogram tracing and the finger pulse signal and determines the pulse wave transit time $t_1-t_0$. The relative change in blood pressure is compared with a predetermined limit value in a comparator 36' which is connected to analyzer unit 34' over a data line 35'. When the relative change in blood pressure drops below the limit value, the comparator 36' generates an activation or deactivation signal which is received by control unit 22' of the hemofiltration machine over a data line 37'.

Control unit 22' is connected over data line 38' to an input unit 39' where the user can specify which measures are to be taken to counteract a sudden drop in blood pressure, as in the case of the hemodialysis machine.

Monitoring device 28' also has an acoustic and/or optical alarm generator 41' which is activated by control unit 22' over a control line 42' when there is a sudden drop in blood pressure.

An absolute sphygmomanometer 43' with an inflatable rubber cuff which is connected to analyzer unit 34' over a data line 44' permits absolute blood pressure readings.

As is the case with the hemofiltration machine described with reference to FIGS. 1 through 3, pulse waves can be detected either on the patient's finger using a photoplethysmograph or with a pressure sensor 46' arranged in the arterial blood inlet line.

What is claimed is:

1. A blood treatment device for extracorporeal blood treatment comprising:
    a) an extracorporeal blood path connecting a subject to the blood treatment device, the blood treatment device having an inlet and an outlet, the extracorporeal blood path carrying blood from the subject to the blood treatment device inlet and from the blood treatment device outlet back to the subject;
    b) a measurement device connected to the subject for continuously measuring a value selected from the group consisting of a pulse wave velocity and a pulse wave transit time;
    c) a correlation device connected to the measurement device, the correlation device adapted to determine a correlative value correlating a blood pressure value to the measured value;
    d) a comparison device connected to the correlation device, the comparison device adapted to compare the correlative value with a predetermined limit and generate a signal when the correlative value is outside the limit; and
    e) a control unit connected to the comparison device, the control unit adapted to selectively initiate, based on a user preference, one of a plurality of changes in the subject's extracorporeal blood treatment in response to the signal.

2. The device of claim 1, wherein the measurement device further comprises:
    i) an electrocardiography device connected to the subject for recording the subject's electrocardiogram;
    ii) a pulse detection device connected to the subject for detecting the subject's pulses;
    iii) a time comparison device connected to the electrocardiography device and the pulse detection device, wherein the time comparison device is adapted to calculate the pulse wave transit time using the time between an R wave from the subject's electrocardiogram ($t_0$) and time ($t_1$) of the pulse corresponding to the R wave.

3. The device of claim 2, wherein the subject's pulse is measured by a device selected from the group consisting of a photoplethysmograph and a pressure sensor in the extracorporeal blood path.

4. The device of claim 3, wherein the subject's pulse is measured by a pressure sensor located upstream of the blood treatment device.

5. The device of claim 2, wherein the correlation device is configured to calculate the blood pressure value from the pulse wave transit time using the equation:

$$P=1/n(m-PWLZ)$$

where:
    P=blood pressure;
    m and n=subject specific parameters; and
    PWLZ=pulse wave transit time.

6. The device of claim 1, wherein the blood treatment device is selected from the group consisting of a hemofiltration device, a hemodialysis device, and a cell separator device.

7. The device of claim 1, wherein the correlation device is adapted to determine a blood pressure correlation value that correlates with the blood pressure and correlate the blood pressure correlation value with the blood pressure value.

8. The device of claim 1, further comprising a NaCl delivery device connected to the control unit, the NaCl delivery device adapted for delivering NaCl solution to the extracorporeal blood path in response to the signal.

9. The device of claim 1, wherein the blood treatment machine further comprises an alarm generator connected to the control unit and adapted to generate an alarm when the blood pressure value is outside the blood pressure limit.

10. The device of claim 9, wherein the alarm generator is selected from the group consisting of an acoustical alarm and an optical alarm.

11. The device of claim 1, wherein the blood treatment device comprises a dialysis unit divided by a semipermeable membrane into a blood chamber and a dialysate chamber, the blood chamber having a blood inlet and a blood outlet, the blood chamber in fluid communication with the extracorporeal blood path, the dialysate chamber having a dialysate inlet and a dialysate outlet, the dialysate chamber connected to a dialysate path, the dialysate path further comprising a balancing device, an ultrafiltration device and an ultrafiltration pump connected to the control device, the ultrafiltration pump adapted to be activated and deactivated in response to the signal.

12. The device of claim 1, wherein the blood treatment machine further comprises a temperature stabilizing unit adapted to set the dialysate temperature to two or more different preset temperatures in response to the signal.

13. The device of claim 1, wherein the blood treatment machine further comprises a device for delivering electrolytes to the extracorporeal blood path in response to the signal.

14. The method of claim 13, wherein the device for delivering electrolytes delivers electrolytes selected from the group consisting of $Na^+$ and $K^+$.

15. The device of claim 1, wherein the blood treatment device further comprises a drug delivery device connected to the control unit and the subject and adapted for delivering blood pressure-stabilizing drugs to the subject in response to the signal.

16. The device of claim 1, wherein the correlation device is further adapted to generate a signal in response to a predetermined change in the blood pressure correlation value.

17. A hemodialysis machine comprising:
a) an extracorporeal blood path connecting a subject to a dialyzer having an inlet and an outlet, the extracorporeal blood path carrying blood from the subject to the inlet of the dialyzer and from the outlet of the dialyzer back to the subject;
b) a measurement device connected to the subject for continuously measuring a value selected from the group consisting of a pulse wave velocity and a pulse wave transit time, the measurement device further comprising a pulse detection device for detecting the subject's pulses, the subject's pulses being measured by a pressure sensor in the extracorporeal blood path;
c) a correlation device connected to the measurement device, the correlation device adapted to determine a correlative value correlating a blood pressure value to the measured value;
d) a comparison device connected to the correlation device, the comparison device adapted to compare the correlative value with a predetermined limit and generate a signal when the correlative value is outside the limit; and
e) a control unit connected to the comparison device, the control unit adapted to initiate a change in the subject's extracorporeal blood treatment in response to the signal.

18. A hemofiltration machine comprising:
a) an extracorporeal blood path connecting a subject to a hemofilter having an inlet and an outlet, the extracorporeal blood path carrying blood from the subject to the inlet of the hemofilter and from the outlet of the hemofilter back to the subject;
b) a measurement device connected to the subject for continuously measuring a value selected from the group consisting of a pulse wave velocity and a pulse wave transit time, the measurement device further comprising a pulse detection device for detecting the subject's pulses, the subject's pulses being measured by a pressure sensor in the extracorporeal blood path;
c) a correlation device connected to the measurement device, the correlation device adapted to determine a correlative value correlating a blood pressure value to the measured value;
d) a comparison device connected to the correlation device, the comparison device adapted to compare the correlative value with a predetermined limit and generate a signal when the correlative value is outside the limit; and
e) a control unit connected to the comparison device, the control unit adapted to initiate a change in the subject's extracorporeal blood treatment in response to the signal.

* * * * *